United States Patent
Taylor

(10) Patent No.: US 10,182,983 B2
(45) Date of Patent: Jan. 22, 2019

(54) CONTAINER

(71) Applicant: De Montfort University, Leicester, Leicestershire (GB)

(72) Inventor: Margaret Joan Taylor, Leicester (GB)

(73) Assignee: De Montfort University, Leicester, Leicestershire (GB)

(*) Notice: Subject to any disclaimer, the term of this patent is extended or adjusted under 35 U.S.C. 154(b) by 0 days.

(21) Appl. No.: 14/959,502

(22) Filed: Dec. 4, 2015

(65) Prior Publication Data

US 2016/0158145 A1   Jun. 9, 2016

Related U.S. Application Data

(63) Continuation of application No. PCT/GB2014/051733, filed on Jun. 5, 2014.

(30) Foreign Application Priority Data

Jun. 7, 2013 (GB) .................................. 1310185.2

(51) Int. Cl.
   *A61K 9/00* (2006.01)
   *A61K 47/42* (2017.01)
   (Continued)

(52) U.S. Cl.
   CPC .......... *A61K 9/0004* (2013.01); *A61K 9/0024* (2013.01); *A61K 38/28* (2013.01);
   (Continued)

(58) Field of Classification Search
   None
   See application file for complete search history.

(56) References Cited

U.S. PATENT DOCUMENTS

2017/0007676 A1   1/2017   Taylor

FOREIGN PATENT DOCUMENTS

DE         4039468 A1     6/1992
WO       199316803 A1     9/1993
(Continued)

OTHER PUBLICATIONS

Moravej et al.; Int. J. Mol. Sci. (2011), 12, 4250-4270; published Jun. 29, 2011.*

(Continued)

*Primary Examiner* — Jeffrey T. Palenik
(74) *Attorney, Agent, or Firm* — Mahreen Chauhdry Hoda; Carolyn S. Elmore; Elmore Patent Law Group, P.C.

(57) ABSTRACT

The present invention relates to a container for an analyte-sensitive gel. When analyte contacts such a gel it causes a gel-sol transition resulting in decreased viscosity of the gel. Such gels can be used for controlling the rate of release of an agent from a reservoir in response to the concentration of an analyte. The container is configured to allow analyte to pass into the container and contact the gel and to allow agent to diffuse out of the container. Such a container may be implantable in the body of a subject and therefore it is preferred if the container is constructed from materials that can be tolerated by the body for a period of time. Advantageously, the container limits the swelling and dilution of gel contained within the container caused by the influx of water into the gel by osmosis. The container therefore maintains the gel in a desired conformation and ensures a predictable release profile of the agent.

18 Claims, 6 Drawing Sheets

(51) Int. Cl.
  A61K 47/36 (2006.01)
  A61K 38/28 (2006.01)
  G01N 33/36 (2006.01)
  G01N 33/66 (2006.01)
(52) U.S. Cl.
  CPC .............. *A61K 47/36* (2013.01); *A61K 47/42* (2013.01); *G01N 33/66* (2013.01); *G01N 2333/4724* (2013.01); *G01N 2333/62* (2013.01); *G01N 2400/22* (2013.01)

(56) References Cited

FOREIGN PATENT DOCUMENTS

| WO | 199501186 | 1/1995 |
|---|---|---|
| WO | 2003006993 A2 | 1/2003 |
| WO | 2008112190 A1 | 9/2008 |

OTHER PUBLICATIONS

Taylor, et al., "In Vivo Study of a Polymeric Glucose-Sensitive Insulin Delivery System Using a Rat Model," Journal of Pharmaceutical Sciences, 99(10):4215-4227, 2010.
Tanna, et al., "The effect of degree of acrylic derivatisation on dextran and concanavalin A glucose-responsive materials for closed-loop insulin delivery," Biomaterials, 27(25):4498-4507, 2006.
Taylor, et al., Glucose-sensitive gel rheology of dextran-concanavalin A mixtures suitable for self-regulating insulin delivery, Pharmaceutical Development and Technology, 15(1):80-88, 2010.
Zurich Artificial Pancreas, retrieved from the internet:URL:https://web.archive.org/web/20121227083918/http://www.renfrewgroup.com/pancreas, retrieved Aug. 26, 2014.
Crepy, "Synthesis of Cellulose Fatty Esters as Plastics-Influence of the Degree of Substitution and the Fatty Chain Length on Mechanical Properties," ChemSusChem, 2(2):165-170, 2009.
Korolkovas, et al., "Theoretical Aspects of Drug Action," Essentials of Medicinal Chemistry, Wiley, pp. 44-81, 1976.
Andersson, "Molecular imprinting: developments and applications in the analytical chemistry field," Journal of Chromatography B, 745:3-13, 2000.
Bruggemann, et al., "New configurations and applications of molecularly imprinted polymers," Journal of Chromatogrphy A, 889:15-24, 2000.
Haupt, et al., "Plastic antibodies: developments and applications," Trends Biotechnol., 16(11):468-75, 1998.
Lis, et al., The Biochemistry of Plant Lectins (Phytohemagglutinins)1, Annu. Review of Biochemistry, (42):541, 1973.
Goldstein, et al., "The Lectins: Carbohydrate-Binding Proteins of Plants and Animals*," Adv. in Carbohydrate Chemistry and Biochemistry, 35:128-341, 1978.
Higuchi, T., "Mechanism of sustained-action medication. Theoretical analysis of rate of release of solid drugs dispersed in solid matrices," Journal of Pharmaceutical Sciences, 52(12):1145-1149, 1963.
Hartman, "Insulin Analogs: Impact on Treatment Success, Satisfaction, Quality of Life, and Adherence", Clinical Medicine and Research, 6(2):54-67, 2008.
Miyake, et al., "Characteristics of Anti-testosterone Antisera Produced by Bovine Serum Albumin Conjugates of 15α-and 15β-Carboxymethyltestosterone: Use of [125I]Iodinated Tracers" Chem Pharm Bull, 38(4):951-955, 1990.
Kussie, et al., "Analysis of the Binding Site Architecture of Monoclonal Antibodies to Morphine by Using Competitive Ligand Binding and Molecular Modeling", The Journal of Immunology, 146(12):4248-4257, 1991.
Carnali, et al., "The Use of dilute solution viscometry to characterize the network properties of carbopol microgels", Colloid Polymer Sci., 270:183-193, 1992.
Fischel-Ghodsian, et al., "Analysis of Drug Release Kinetics from Degradable Polymeric Devices", Journal of Drug Targeting, (1):51-57, 1993.
Brange, "Galenics of Insulin: The Physico-Chemical and Pharmaceutical Aspects of Insulin and Insulin Preparations",1-103:1987.
Kim, et al., "Modulated insulin delivery from glucose-sensitive hydrogel dosage forms," Journal of Controlled Release, 77:39-47, 2001.
Tanna, et al., "Glucose-responsive UV polymerised dextran-concanavalin A acrylic derivatised mixtures for closed loop insulin delivery", Biomaterials, 27:1586-1597, 2006.
Tanna, et al., "Covalent coupling of concanavalin A to a Carbopol 934P and 941P carrier in glucose-sensitive gels for delivery of insulin", Journal of Pharmacy and Pharmacology, 54:1461-1469, 2002.
Tanna, et al., "A Covalently Stabilised Glucose Responsive Gel Formation with a Carbopol Carrier", Journal of Drug Targeting, 10(5):411-418, 2002.

* cited by examiner

CONTAINER

RELATED APPLICATIONS

This application is a continuation of International Application No. PCT/GB14/051733, which designated the United States and was filed on Jun. 5, 2014, published in English. This application also claims priority under 35 U.S.C. § 119 or 365 to Great Britain Application No. 1310185.2, filed Jun. 7, 2013. The entire teachings of the above application are incorporated herein by reference.

The present invention relates to a container.

WO 03/006993 discloses a gel which, in one embodiment, comprises dextran and concanavalin A (ConA). Terminal glucose residues of dextran bind to ConA, resulting in the formation of a high viscosity gel. Reversal of this binding occurs when free glucose competes with the dextran glucose residues for binding to ConA, such that the gel loses viscosity. Thus, the gel is sensitive to the amount of free glucose with which it is brought into contact. As such, the gel can be used as a drug delivery system using an antihyperglycaemic drug such as insulin. In normal levels of glucose, dextran binds ConA and the gel can be used as a barrier to limit the release of insulin from a reservoir. However, when the level of glucose rises, the degree of binding falls allowing insulin to be released from the reservoir at an increased rate. In a physiological situation, the release of insulin will result in the level of glucose falling which in turn will cause the degree of binding to increase, thereby decreasing the rate of insulin release. Thus, the drug delivery system forms a "closed loop" system which mimics the activity of a normally-functioning pancreas, with insulin being released when required (when glucose causes the gel to undergo gel-sol transition) and retained when not required (when the lack of glucose causes the gel to undergo sol-gel transition).

A problem of gels of this type is that, when placed in the body, they absorb water by osmosis thus becoming diluted. There are several problems associated with gel dilution. For example, a first problem is that when the gel is diluted, the component parts (e.g. Dextran and ConA) cease to be in close proximity. As a result, the cohesion that fosters a tightly bonded gel in the absence of glucose is reduced. Therefore, the difference between the gel state and the glucose-rich sol state is lost i.e. the gel loses the ability to undergo gel-sol and sol-gel transition (although some competitive binding may still occur) and can no longer provide differential release of a drug. A second problem is that the reduction in viscosity caused by gel dilution raises the permeability of the gel. If the gel is being used as a barrier to a drug, a reduction in viscosity and an increase in permeability may result in unwanted, uncontrolled release of the drug. A third problem is that when the gel is diluted, the geometry of the gel changes so that the path length (through the gel) increases. If the gel is being used as a barrier to a drug, the increased path length would slow the rate of delivery of the drug. Although the effects of the second and third problems oppose each other, the net effect is unpredictable.

According to a first aspect of the present invention, there is provided a container for a gel comprising first and second gel forming moieties which bind reversibly to one another to form a gel, said binding being sensitive to the level of an analyte; the container allowing movement of the analyte into and out of the gel and being capable of resisting an internal pressure of at least about 250 mbar (25 kPa) to limit swelling of the gel caused by influx of water into the gel by osmosis.

According to a second aspect of the invention, there is provided a container containing a gel, wherein (a) the gel comprises first and second gel forming moieties which bind reversibly to one another to form a gel, said binding being sensitive to the level of an analyte, and (b) the container allows movement of the analyte into and out of the gel and limits swelling of the gel caused by influx of water into the gel by osmosis.

In the second aspect of the invention, the container may be capable of resisting an internal pressure of at least about 250 mbar (25 kPa).

Generally, the container may have a size and shape which is capable of containing a gel and limiting the expansion of the gel as it absorbs water by osmosis, thereby limiting or preventing dilution of the gel. The internal dimensions of the container will depend on the size and dimensions of the gel to be contained and the amount of expansion which is deemed to be acceptable. In one embodiment of the invention, the container is provided as part of a delivery system for an agent such as a drug, which can be inserted into the body of a human or animal subject. In this case, the external dimensions of the container will be limited by the anatomy of the human or animal subject and the manner in which the agent is to be delivered.

The dimensions of the gel to be contained will depend on a number of factors. For example, a gel contained within the container of the invention may be used to control the release of an agent such as a drug. This may be achieved by using the gel to form a relative barrier to a reservoir of the agent. By "relative barrier", it is meant that the gel does not completely eliminate diffusion of the agent. Generally, the characteristics of the gel are such that a basal dose of the agent is released through the gel, even when the gel is in the gel state i.e. the agent can diffuse out only slowly. Thus, when the gel is in the gel state, the agent is substantially contained in the reservoir. When the analyte contacts the gel and causes gel to sol transition, the viscosity of the gel decreases and the agent is released by diffusion through the gel more quickly, thereby boosting the dose of the agent delivered. In such cases, the required rate of diffusion of the agent through the gel will be taken into consideration when determining the dimensions of the gel. Solutes diffuse from areas of high concentration to areas of low concentration. The skilled person will understand from Fick's first law of diffusion that the rate of delivery is directly proportional to the area through which a solute can diffuse and the concentration of the solute. The rate of delivery is inversely proportional to the path length (i.e. the distance through which the solute must diffuse). The skilled person will determine the appropriate dimensions for the gel accordingly.

Preferably, gels of no more than about 10 mm in thickness are used in a container of the invention. The thickness of the gel may be no more than about 5 mm. In some embodiments, the thickness of the gel may be from about 1 mm to about 4 mm inclusive. In some embodiments, the gel is no more than about 2 mm thick or no more than about 1 mm thick. In some embodiments it is preferable if the gel is about 1 mm thick. The container of the present invention can prevent the thickness of the gel exceeding the desired thickness by osmotic dilution, even when the gel and container are situated in an aqueous environment (such as the body of a subject) for an extended period of time. Preferably, the container maintains the thickness of the gel for the duration of the time in which the gel and container are situated in the aqueous environment.

The container of the present invention advantageously limits the swelling and dilution of a gel contained within the container caused by the influx into the gel of water by osmosis.

As the gel absorbs water and expands within the container, the pressure inside the container increases until the gel cannot absorb any more water. If the container is too weak, the pressure may cause the container to buckle or rupture. This may be followed by a decrease in pressure due to deformation of the container. It is important that the container is able to resist deformation as far as possible to prevent dilution of the gel as discussed above.

The container limits the expansion of the gel caused by the osmotic influx of water by physically restraining the gel. This ensures that the path length through the gel remains relatively constant, with the result that diffusion through the gel (in either the gel or the sol state) remains at the desired rate. By limiting expansion of the gel, the container prevents the gel absorbing excessive amounts of water which cause the gel to become diluted, thereby ameliorating the problems associated with dilution discussed above. Preferably, the container is capable of preventing the gel becoming diluted by a maximum of about 20%, more preferably by a maximum of about 15%, still more preferably by a maximum of about 10%, still more preferably by a maximum of about 5% and most preferably by a maximum of about 1%. Holding a gel in the container of the invention, allows the gel to remain effective at precisely controlling the delivery of an agent in response to the level of an analyte.

Preferably, the container has a wall that is permeable or semipermeable. The container must allow the analyte to which the gel is sensitive, to pass through it in order to contact and enter the gel. In addition, the container is preferably capable of preventing the escape from the container of the gel components and the entry into the container of, for example, enzymes in the peritoneal fluid. In certain embodiments, the gel is used to form a relative barrier between a reservoir of an agent, such as a drug, and the area to which it is to be released, such as the body of a subject. The container may also be configured to allow release of the agent. In certain embodiments, the container is configured to allow the release of insulin, including hexameric insulin having a molecular weight of approximately 40 kD. In some embodiments, at least one of the container walls or a component or layer thereof comprises a number of pores. For example, one or more walls may comprise a porous membrane, for example a cellulose membrane. Preferably however, the pore size used is larger than the minimum size that would allow the analyte to diffuse into the container and the agent to diffuse out of the container. This is because the size of the pore can limit the rate of diffusion. In a preferred embodiment, the diameter of the pores in one or more walls forming the container or in a component or layer thereof is from about 10 μm to about 0.01 μm inclusive, or from about 5 μm to about 0.05 μm. The diameter may be about 0.05 μm, about 0.04 μm, about 0.03 μm, about 0.02 μm or about 0.01 μm. The diameter may be smaller provided that release of the agent (where present) and influx of the analyte is not affected.

Preferably, the container is constructed from one or more materials which, when placed inside the body of a subject, can be tolerated by the body for a period of time. Examples of such materials include polycarbonate, reinforced porous cellulose, titanium and stainless steel. Containers according to the invention are expected to remain inside the body for a time period of the order of months or years. It will be appreciated that if the container is to be placed inside the body of a subject, the components of the container should be sterilised and assembled in an aseptic environment. Preferably, the container can remain inside the body for 6 months, more preferably 12 months, even more preferably 18 months and most preferably 2 years or longer.

In one embodiment, the container has top and bottom walls joined by one or more side walls. These side walls may or may not be permeable to the analyte and may or may not be permeable to the agent. The side walls may, for example, define a generally rectangular or circular enclosed space. In this embodiment, the top and bottom walls complete the container to form a cavity in which a gel may be held. One or both of the top and bottom walls of the container can comprise one or more substantially planar grids. Such grids allow the analyte to pass into the container and contact the gel contained therein. Similarly, the grids allow the release of agents from the container. The grids also reinforce the structure of the container and keep the layer of gel flat. The grids can, in some embodiments, be made from a different material to the material from which the rest of the container is made. For example, the container side walls may be made from polycarbonate, and the grids may be made from an inert metal such as stainless steel or titanium.

In some embodiments, 2, 3, 4 or more grids may be used in series to form part of the top and/or bottom walls to help reinforce the structure of the container and keep the gel layer flat. In certain embodiments, spacers may be used to separate multiple grids. The components of the container may be secured together by any suitable means. For example, an outer ring may be secured to a central body using screws, the other components being trapped between the outer ring and central body. In some embodiments, the outward facing side of the grids may be covered by a smooth, permeable or semipermeable material such as porous cellulose or polycarbonate membrane. This membrane preferably comprises pores having a diameter of about 10 μm. In this way, abrasion which could be caused by the grids rubbing against the body of a subject in which the container may be placed can be prevented, while still allowing the analyte to pass into the container and the agent, where present, to pass out of the container. Additionally or alternatively, the outer surfaces of the container including the grids may be made, coated or treated with agents such as biocompatible polymers to improve the interaction with the body.

In some embodiments, the container is adapted to contain two separate layers of gel. It will be appreciated that when two layers of gel are used, the container is adapted to restrict the expansion of each gel layer. This may be achieved using one or more pairs of grids between which each gel layer can be trapped. In such embodiments, both the top and bottom walls of the container are preferably permeable to the analyte, and where present, the agent. This allows analyte to enter the container through the top wall and contact a first layer of gel. Analyte can also enter the container through the bottom wall and contact a second layer of gel. If the container is adapted to release an agent, this agent may be stored in a reservoir situated between the first and second gel layers. Thus, when the analyte causes the gel to undergo gel-sol transition, the agent can be released through both the top and bottom walls of the container. This doubles the surface area for diffusion thereby allowing a larger dose of agent to be released.

In a preferred embodiment, the container is made substantially from a rigid, smooth, porous material. In this embodiment, a layer of gel may be held between an outer rigid porous sleeve and an inner rigid porous sleeve forming the container. Such sleeves may be made from any material which is rigid enough to resist the force generated by the expansion of gel contained caused by the osmotic influx into the gel of water. Advantageously, the container of this embodiment preferably does not require screws or gaskets, and may require fewer parts and seals compared to other embodiments of the present invention. The analyte is able to pass through the outer sleeve in order to contact the gel. In some embodiments, an agent may be stored in a reservoir situated within the inner sleeve. In some embodiments, the container may have a substantially cylindrical, pebble-like or even spherical shape. It is preferable for the container to have rounded edges as this provides improved comfort when the container is situated in the body of a subject. Such a configuration may prevent or limit the development of adhesions, inflammation and/or hernias. The inner sleeve and/or the outer sleeve may be permeable to the agent such that, when the analyte causes the gel to undergo gel-sol transition, the agent can be released from the container. The agent may be released through sequentially, the inner sleeve, the gel and the outer sleeve. It will be appreciated that if a layer of gel is positioned between cylindrical inner and outer sleeves, and an agent is stored in a reservoir within the inner sleeve, the container may comprise top and bottom walls which are impermeable to the agent, so that agent can only be released through the gel. Any material having acceptable levels of porosity and rigidity may be used to construct the sleeves. For example, suitable materials for the sleeves include cellulose ester blends of the type used in osmotic pumps available from http://www.alzet.com/. It will be understood by the skilled person that there are number of equally valid configurations for the gel, the sleeve and, where present, the agent. These should all be considered to be within the scope of the present invention.

The container of the first aspect may contain a gel. As mentioned, the gel useful in the invention comprises first and second gel-forming moieties which bind reversibly to one another to form a gel, wherein said binding is sensitive to the level of an analyte. The gel may be a reversible gel in which the interactive ligand pair (first and second moieties) are retained within the gel (i.e. their leach to the surroundings is prevented). In addition, phase separation of the components during the liquid stages of the gel-sol cycles is preferably prevented, thus ensuring the juxtaposition of the first and second moieties and increasing the life of the composition.

The first moiety preferably binds to the analyte and to the second moiety. In this way, the analyte will compete with the second moiety for binding to the first moiety. This will induce the transition from gel to sol as the bonds between the first and second gel forming moieties are broken. This in turn will reduce the viscosity and increase the permeability of the gel, allowing an agent, where present, to diffuse through the gel at an increased rate.

The first and second moieties can be any moieties which can bind reversibly together to form a gel. It is preferred if the first moiety is a molecule which binds to at least part of the second moiety to bind the second moiety together, and the second moiety is a macromolecule which, when bound together, forms a gel. However, both the first and second moieties could contribute equally to gel formation. Preferably, the sensitivity of the gel to the level of said analyte arises because the first gel-forming moiety also binds to the analyte. Thus, the analyte competes with the second gel-forming moiety and, when the concentration of the analyte is sufficiently high, will prevent binding of the first and second gel-forming moieties, resulting in a decrease in the viscosity of the gel. As is described in more detail below, this decrease in viscosity can be used to release an agent such as a drug.

Bonding between the first and second moieties is caused by non-covalent forces such as hydrophobic, ionic, hydrogen bonding forces and the like. These interactions have been well studied in the art and their effects on molecular affinity and recognition are described, for example in Korolkovas et al, "Essentials of Medicinal Chemistry", pp 44-81 Wiley, 1976. Such reversible interactions are exemplified by the interaction between an enzyme and its substrate or a competitive inhibitor thereof; and antibody with its antigen, or a drug receptor site and its drug.

The first moiety may be any of a number of well-known entities which exhibit molecular recognition and reversible binding of micro-or macromolecules. The first moiety may be a natural binding protein, such as an antibody, an enzyme, a regulatory protein, a drug receptor site or the like. It is also possible to use synthetically modified binding molecules, such as chemically modified proteins. Such modified proteins sometimes have increased or decreased affinities for their substrates when compared to their natural unmodified counterparts. The first moiety may be a receptor built by imprinting and similar techniques (Andersson, *J Chromatogr B Biomed Sci Appl.* 2000 Aug. 4: 745(1):3-13; Bruggemann et al, *J Chromatogr A.* 2000 Aug. 11; 889(1-2):15-24; Haupt & Mosbach, *Trends Biotechnol* 1998 November; 16(11):468-75).

In some embodiments, the analyte is a carbohydrate, such as a sugar such as glucose. The first moiety may be, for example, an enzyme that binds the second moiety but that has been synthetically altered to remove its enzymatic activity. Alternatively, the first moiety may be a phenyl boronic acid polymer. However, it is preferred if the first moiety is a lectin. Lectins are carbohydrate-binding proteins of plants and animals with a wide variety of specificities for carbohydrates, (Lis et al, *Ann. Review of Biochemistry,* 42, 541 (1973); Goldstein & Hayes, *Adv. in Carbohydrate Chemistry and Biochemistry,* Vol. 35, Tipson and Horton, eds. (Academic Press, New York, 1978, pp. 128-341)). For example, ConA, a Jack Bean lectin, has specificity for α-D mannopyranose and α-D glucopyranose; soybean lectins are specific for α- and β-D-N-acetylgalactoseamine and α-D-galactose units, and wheat germ lectin is specific for β-D-N-acetyl glucosamine. Other lectins that may be used include the pea (*Pisium sativum*) lectin and mannose binding protein. These binding pairs may form the first and second moieties of a gel useful in the invention. In a preferred embodiment, the first moiety is a lectin, and the second moiety is a gel-forming macromolecule which binds to the lectin, and which may be a carbohydrate polymer or polysaccharide, preferably containing glucose, fructose or mannose moieties. Examples include branched starches, dextrans, mannans, and levans, or synthetic carbohydrates such as ficoll-400, a synthetic polysucrose, and a synthetic polymer with pendant carbohydrate or sugar moieties. Preferably the first moiety is concanvalin A and the second moiety is dextran.

In one embodiment, blue dextran is used (Sigma) for the second moiety. Blue dextran is available in two molecular weights (40 K and 2 M), and comprises dextran covalently bonded to reactive blue. Each dextran molecule has many dye moieties bonded to it, and the molecule is blue and has free amine groups from the dye which are available for coupling. When coupling is done with blue dextran, the product is blue. This provides a qualitative and quantitative assessment of the success of coupling where the blue dextran has been bonded as a derivatised component to produce a polymer of conjugate for versions of the glucose sensitive system.

The first and second moieties may be provided in the form of a copolymer. This may be made by polymerising prepared derivatives of the first and second moieties. At its simplest, this can make a linear polymer bearing both moieties. Any type of polymer backbone produced by any relevant polymerisation technique is suitable for use in this embodiment. In one embodiment, the methacrylate derivatives of lectin and polysaccharide (synthesised first from the raw lectin and polysaccharide, using a reaction with methacrylic anhydride) are polymerised to make an acrylic backbone polymer, carrying the lectin and polysaccharide as pendants.

Dextran is capable of methacrylate derivatisation (i.e. in the pre-polymerisation stage with methacrylic anhydride) at many points along its length, the number depending on conditions, since each hydroxyl group of every glucose unit in the dextran chain, is potentially susceptible to methacrylation. Accordingly, dextran moieties can permanently cross link the linear copolymer, producing a range of three-dimensional networks simply because it can start forming polymer chains at any point at which it has a methacrylate modification. Unless the degree of cross linking is very high, the ensuing products are likely to be flexible and gelatinous because of the length and mobility of dextran. Concanavalin A can also be multi-methacrylated, but because this molecule is globular, the product may be an aggregate and not a gel in which flexible networking extends throughout.

The fundamental character of products made by a polymerisation process such as the one described above is hydrophilic, but, in cases where the polymerisation product becomes too large and complicated to remain soluble, the product merely swells in water and does not form a solution (e.g. soft contact lenses are an example of a product made from a hydrogel that swells but does not dissolve). The permanent links dictate the major characteristics of the product in terms of its viscoelastic qualities, and so those products which have less derivatisation of the dextran and concanavalin A (for example) will be viscous liquids, while those which have extensive modification and thus allow complicated cross linking, will be solid hydrogels.

However, the interactive ligands are able to connect across the polymer chains non-covalently producing temporary bonding additional to any permanent bonds made during polymerisation. It is these which are crucial in terms of the reversible binding of the gel because, when in contact with the analyte, e.g. free glucose, the temporary bonds will be dismantled. When this happens, there will be a change in the properties of the product and it will become more permeable, as the notional pores throughout the lattice open up and leave only the permanent cross links. If the derivatisation and consequent permanent cross linking of the gel has been appropriately low, a viscous liquid can result when all of the permanent and temporary linking is in place. When the analyte is added, this liquid will lose viscosity and, because the reaction is reversible, this gel-sol change can be dependent on the concentration of analyte that has diffused into the gel.

Where the first and second gel-forming entities are not copolymerised, each component is multivalent in order that a three dimensional network or matrix results (and at least one component must have a valency greater than two, since two divalent interactants produce a linear arrangement).

In a gel comprising lectin and dextran which are not attached to one another or to other particles, the lectin is in its naturally tetravalent form which can dissociate into stable dimers at some pH values. These dimers are obviously smaller and are at a greater risk of loss from the gel. The combination of the tetravalent concanavalin A and the multivalent (branched) dextran produces a gel, which consists of a three dimensional network stabilised with only temporary bonds. However, the components can gradually leach away when in the sol state: phase separation may not be obvious but may contribute to progressive loss of action after several cycles.

However, when the interactive components are copolymerised or attached to particles, each component could be monovalent, and this would still form a gel. Accordingly, certain gels described herein do not require first and second gel-forming moieties which are multivalent. In a preferred embodiment, lectin dimers (or tetramers stabilised by binding onto the framework) can be used. Dextran may be substituted with a variety of other glucose bearing entities, including simple pendant glucose. However, single pendant glucose may reduce the flexibility of the resulting gel and in fact, some permanent cross linking with dextran might be remain useful to give flexibility and prevent leaching away in the sol phase. The gel may be as described in WO 03/006993.

The container and gel may form part of a delivery system for an agent such as a drug. The gel-sol transition of the gel composition described herein in response to raised levels of the analyte, can be used to release an agent, preferably which is a drug that acts to lower levels of the analyte. The agent may be contained either (a) within the gel composition or (b) in a reservoir with the gel composition forming a relative barrier between the reservoir and the area to which the agent is to be released. "Drug" is intended to mean any active agent, the delivery of which has a desired therapeutic or prophylactic effect.

The binding of the first and second gel-forming moieties, and hence the viscosity of the gel composition, is sensitive to the level of the analyte. This change in viscosity can be used to control the permeability of the gel to the agent. Thus, the gel compositions described herein can form a relative barrier to a reservoir of an agent. Release of the agent from the container is governed by the viscosity of the gel, i.e. the level of the analyte. Alternatively, the drug can be contained within the gel itself. It is preferred if the gel composition is sensitive to glucose (e.g. a ConA/dextran-based gel) and the drug to be released is an anti-hyperglycaemic drug such as insulin. It is also possible for a glucose-sensitive gel to be used to control the release of any agent, the release of the agent being controlled by the administration of glucose to a patient.

When the delivery system is used to deliver insulin, it is preferred if it is used intraperitoneally because this allows glucose to reach the system quickly and for insulin to be released quickly, than say if the system were used subcutaneously. In addition, peritoneal fluid has a glucose level which mirrors blood glucose levels. That is not to say that the system cannot be used subcutaneously or even externally-the location should be selected so as to suit the condition to be treated and the agent to be released.

Preferred features of each aspect of the invention are as for each of the other aspects mutatis mutandis. The prior art documents mentioned herein are incorporated to the fullest extent permitted by law.

The invention will now be described in more detail with reference to the accompanying drawings and in the following non-limiting examples. The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

Figure 1A:
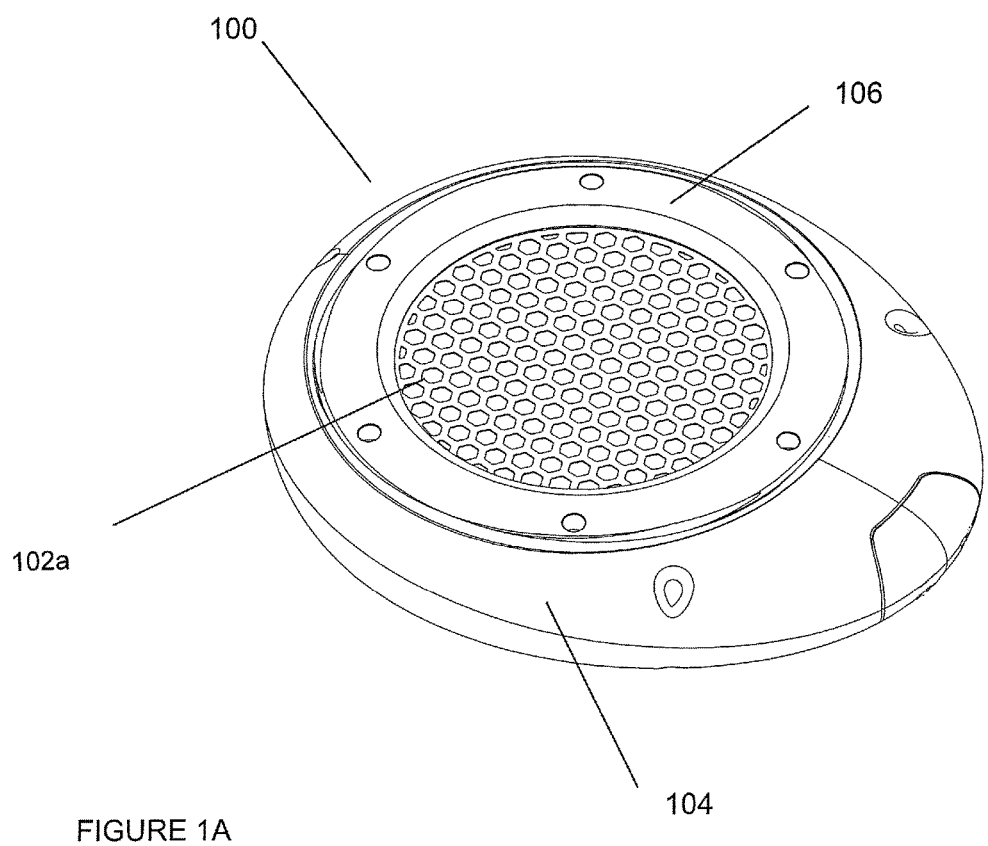
FIG. 1A is a perspective view of one embodiment of a container of the invention.
Figure 1B:
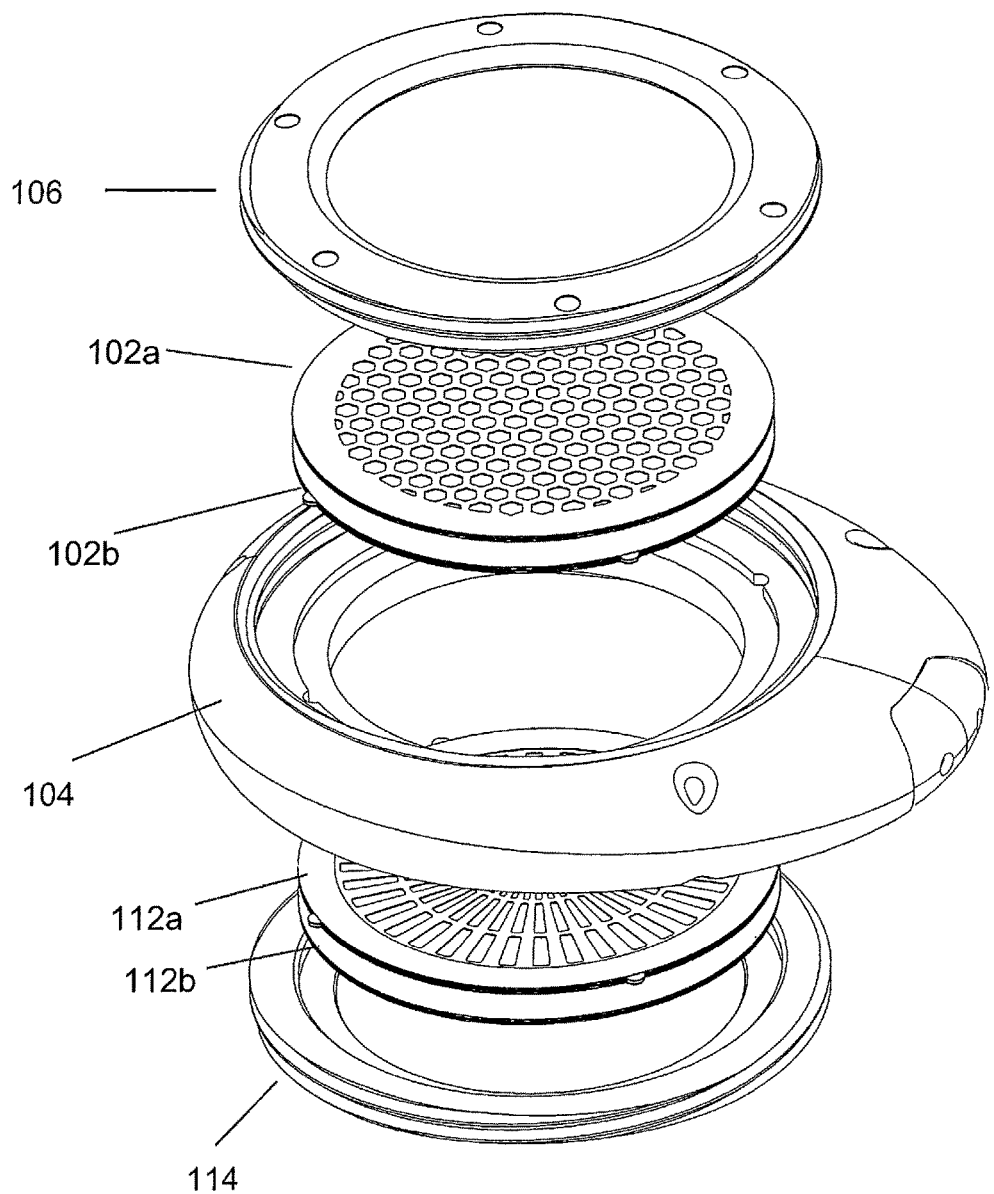
FIG. 1B is an exploded view of the container.

FIG. 1A shows a perspective view of an embodiment of a container (100) of the invention. FIG. 1B shows an exploded view of the same embodiment. The container (100) comprises a side wall (104), and two pairs of grids (102a and 102b) and (112a and 112b) which are riveted to the side wall (104) with annular clamps (106) and (114). The honeycomb grid design shown may be used to maximise the ability of glucose to access to the gel by diffusion. The slatted grid design shown may be used to prevent through access for a needle (e.g. when the device is sutured in place) while allowing insulin held in a reservoir to access the gel. The embodiment shown allows for two separate gels to be held within the container. A first gel may be held between the grids (102a and 102b), and a second gel may be held between grids (112a and 112b). This embodiment therefore allows for an agent to be stored in a reservoir located between the two pairs of grids. The agent can thus be released from both the top and bottom the container as described above. In this embodiment, the gel may be sandwiched between cellulose membranes (not shown) in order to stop the gel escaping through the grid.

Figure 2:
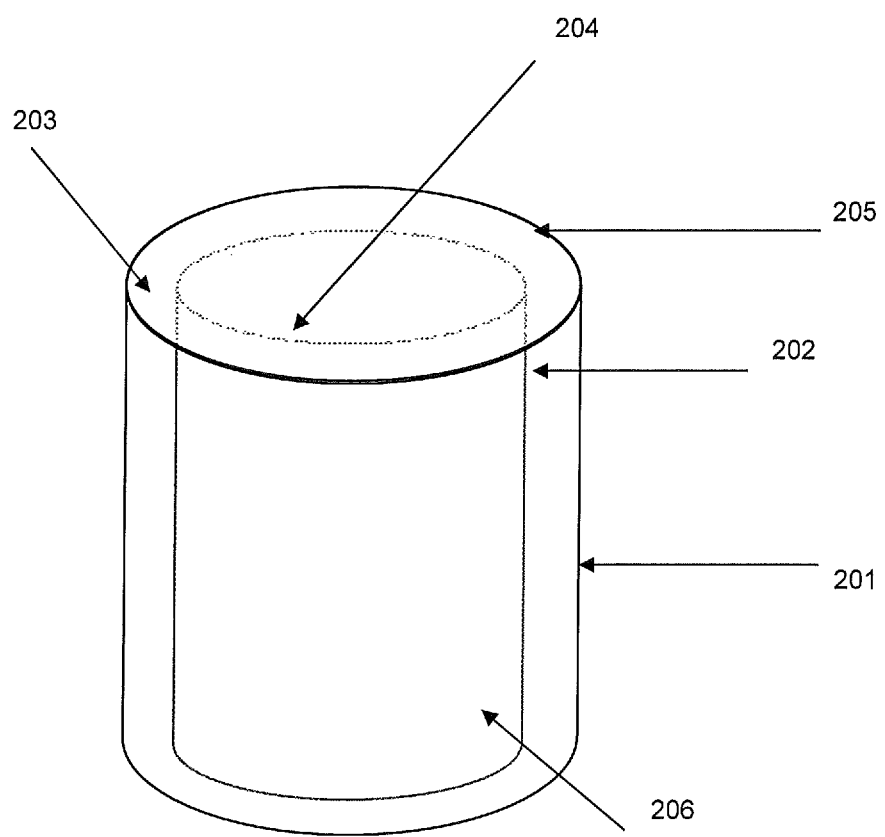
FIG. 2 shows another embodiment of a container of the invention.

FIG. 2 shows another embodiment of the present invention. A cylindrical layer of gel (203) is held between an outer rigid sleeve (201) and an inner rigid sleeve (202). An agent can be stored in a reservoir (204) within the inner sleeve (202). The top wall (205) and the bottom wall (206) are impermeable to the agent. When the gel (203) is in the gel state, it forms a relative barrier to the agent such that the agent diffuse slowly from the container delivering only a basal dose. Analyte can pass through sleeve (201) and contact the gel (203) thereby causing the gel to undergo gel-sol transition. The agent is then able to diffuse more rapidly through sequentially sleeve (202), the gel (203) and the outer sleeve (201) to be released from the container at a greater dose rate. When the level of analyte decreases, the gel (203) undergoes sol-gel transition and the agent is once again substantially confined to the reservoir (204).

EXAMPLE 1

To measure the pressure generated in a container containing a gel, an experimental rig was set up.

The gel was sandwiched between two membranes and then clamped between two stainless steel grids using a polycarbonate support and clamp screws to form a gel container.

Gaskets were used to protect the gel during clamping. The gel was spread as evenly as possible to exclude air spaces and a microfine pressure transducer (Samba Preclin 420 LP version) was placed in the gel using a fine, hollow needle. An identical torque (5 mN) was imposed on each of the clamp screws. Conforming gasket material was used to seal any spaces around and beyond the rims of the grids as the container was clamped.

Grids with surface area ranging from 27 to 90% were used where the 90% grid had the least metal and the greatest exposed surface area (for the underlying cellulose membrane).

The gels were made by mixing dextran D500 and con A in various ratios expressed as percentage inclusion in plain mixtures. The 10%:10% gels were used as both a plain mixture and as a polymerised product.

The container was placed in a bathing fluid and the pressure inside the container was measured.

The variables were the gel formulations, grid type and glucose concentration in the bathing fluid. The results reported below were from experiments at 20° C., on the basis that this gives the largest change between the glucose and glucose-free viscosities. The experiments were conducted with and without glucose in the soak solution, to see the effect of glucose-induced liquefaction on the developing pressures.

Effect of Grid Strength

Figure 3:
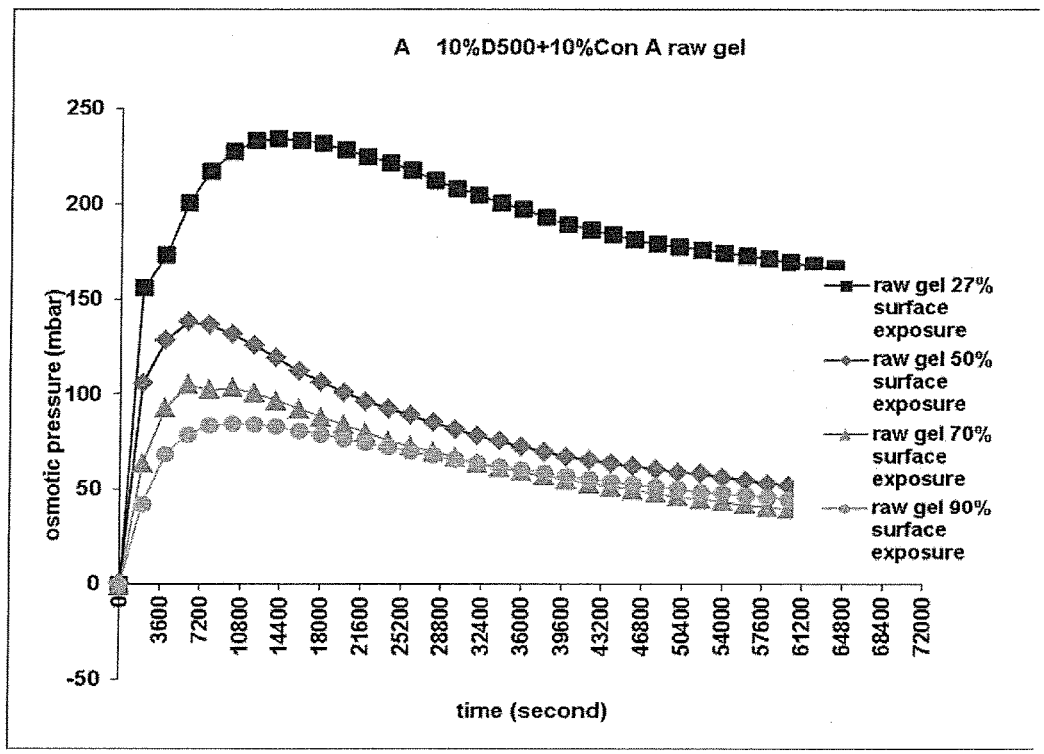
FIG. 3 shows a graph of the internal pressure measured in four gel-containing test containers immersed in distilled water as described in Example 1.

The 10%:10% glucose-free gel results are shown in FIG. 3. Increasing the membrane exposure using grid meshes ranging from 27% to 90% surface exposure lowered the peak and final pressure built up in the gel compartment. Pressure subsided with the weaker grid systems falling to a lower level than with the strongest one. With the strongest grid (27% exposed surface), the pressure reached a substantially higher value than with the other three and then lost less pressure. For all systems, there was no visible sign of grid deformation either in the course of or after the experiment, and on inspection, the gel was always present but with the weaker gels there were signs of seepage past the gaskets.

The explanation seems to be that, as water is imbibed and pressure starts to build, elastic deformation occurs and the pressure rise is reversed. For the weaker grid systems, as the central part of the grid flexes to a greater extent (though elastically and not visibly in these cases), it destabilises the perimeter seal to allow seepage and causes additional pressure loss. The extra volume created would allow additional water in to dilute the gel further.

Effect of Glucose at 1% w/v

Figure 4:
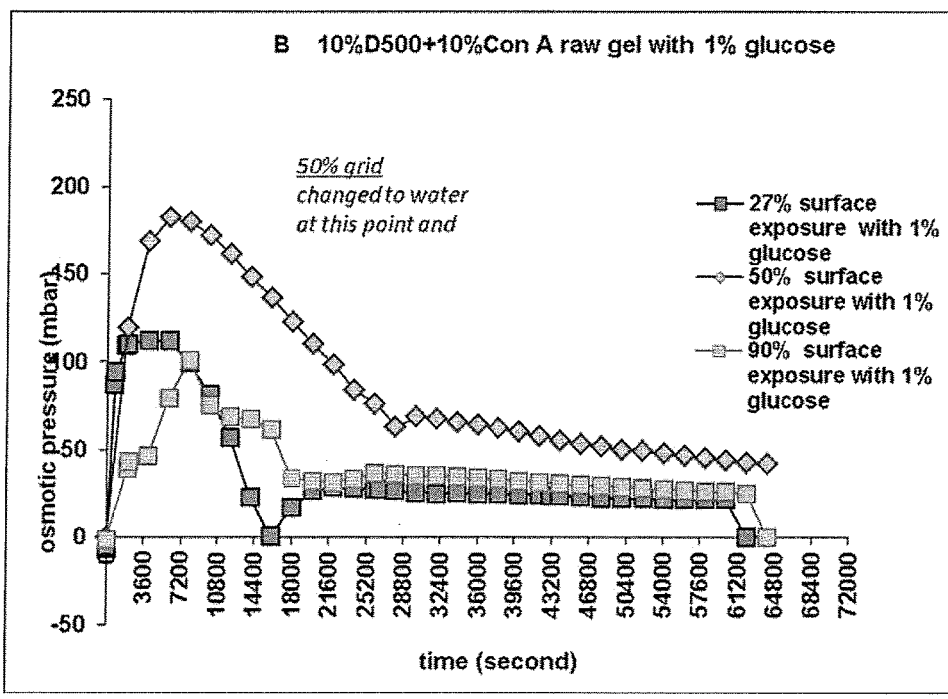
FIG. 4 shows a graph of the internal pressure measured in four gel-containing test containers immersed in a 1% glucose solution as described in Example 1.

The effect of glucose at 1% w/v is to completely liquefy the gel. Here the glucose-free gel was again used to fill the device but the soaking solution contained glucose solution instead of water. In the glucose systems, the pressure again starts to rise steeply as water enters the gel, with the strongest grid system pressure rising fastest initially but then dropping sharply. In this case, the 50% grid typically maintained the pressure for longer before also dropping sharply (FIG. 4).

Explanation

The osmotic pressure should not be greatly affected by the presence of glucose in the bathing fluid in the timescale of the observation, because although much more osmotically active than the gel, its concentration rapidly equilibrates across the cellulose membrane to produce approximately 1% w/v free glucose throughout. After this point, only the gel components contribute to the tendency to imbibe water, as in the glucose-free system. Again the weaker steel grids temporarily deform with excess water intake probably causing seepage and pressure drop. However, in the glucose systems the gel, already diluted by water uptake, liquefies because of dextran displacement as soon as glucose diffuses into it from the bathing solution.

Glucose occupies receptor sites in the lectin (possibly as osmotically inactive bound glucose), displacing dextran moieties, and is in an equilibrium with unbound 1% glucose. However, since we know that the receptor interaction does not preclude the dextran acting osmotically as single molecules (see discussion of formulations below), it is not surprising that this does not result in a rise in pressure. The pressure in the glucose systems never reaches the high values of the glucose-free systems and falls off more steeply and at lower peak pressures. It seems likely that the perimeter distortion again allows seepage and that this is exacerbated for the glucose-induced liquefaction of the gel to a sol. The interplay between these effects may explain why the 50% system proved more successful for these liquid systems. Thus whereas the strong grid worked well in the gels system with plain water, it was not successful in preventing pressure loss where a sol was produced by the glucose action on the gel. This is important because it implies system failure. It was of interest then to see the effect of a lower concentration of glucose.

The Effect of Glucose Concentration

Figure 5:
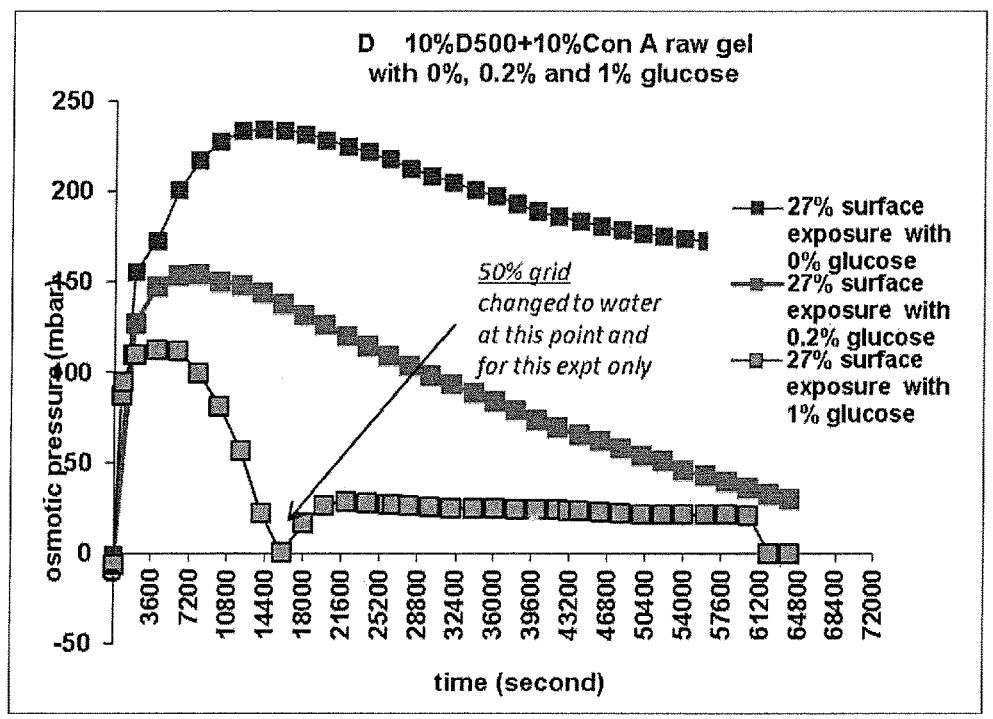
FIG. 5 shows a graph of the internal pressure measured in a 27% gel surface-exposed container immersed in 0%, 0.2% and 1% glucose solutions as described in Example 1.

For the most robust grid (27%), two levels of glucose were added to the bathing solution. The lower level, 0.2% w/v, is about twice normal blood glucose level and therefore relevant for the operation of the gel controlling the insulin release in a fully assembled device. There is some softening of the gel at 0.2% glucose (viscosity measurements not shown here) but it remains gelatinous compared to the effect of 1%. The pressure reached by the 0.2% system is intermediate between the 0 and 1% systems (FIG. 5) and the inference is that the partial conversion to the sol has allowed some seepage compared to the 0% system but not as much as with the 1% system which has a very low viscosity similar to water.

EXAMPLE 2

This example describes an experiment designed to test the suitability of a closed loop glucose sensitive insulin delivery device in vivo. The experiment was also designed to test and develop the surgery and engineering required to create such a device and insert it into a test subject, in this instance a pig.

Experimental Methods

A device was designed and engineered such that a water tight reservoir was closed on each side with a diffusing membrane composed of a biomaterial that is glucose-sensitive. This material is a very lightly cross-linked polymeric gelatinous formulation and lowers reversibly in viscosity when in contact with glucose, thus becoming more permeable to insulin. The construction of the device keeps the gel in a flat layer, resisting osmotic expansion. The gel therefore changes state only in response to glucose.

The device was sutured in place in the peritoneal cavity and its refill circuit tunneled through the dorsal musculature. Each end of the circuit was closed with a needle-accessible port and was sutured in place subcutaneously. A venous access port was place in a feed vein to the jugular for sampling and administration throughout the study. At surgery, the device had already been filled with saline and all implantable components had been hypochlorite-sterilised. The pig was allowed to recover and heal, was rendered diabetic with 2-3 iv low doses of streptozotocin until blood glucose levels were >20 mmol/L and then soluble insulin introduced into the device. Once the diabetes was starting to be controlled, glucose challenges (normally 60 g) were given orally and charted.

Results and Discussion

Figure 6:
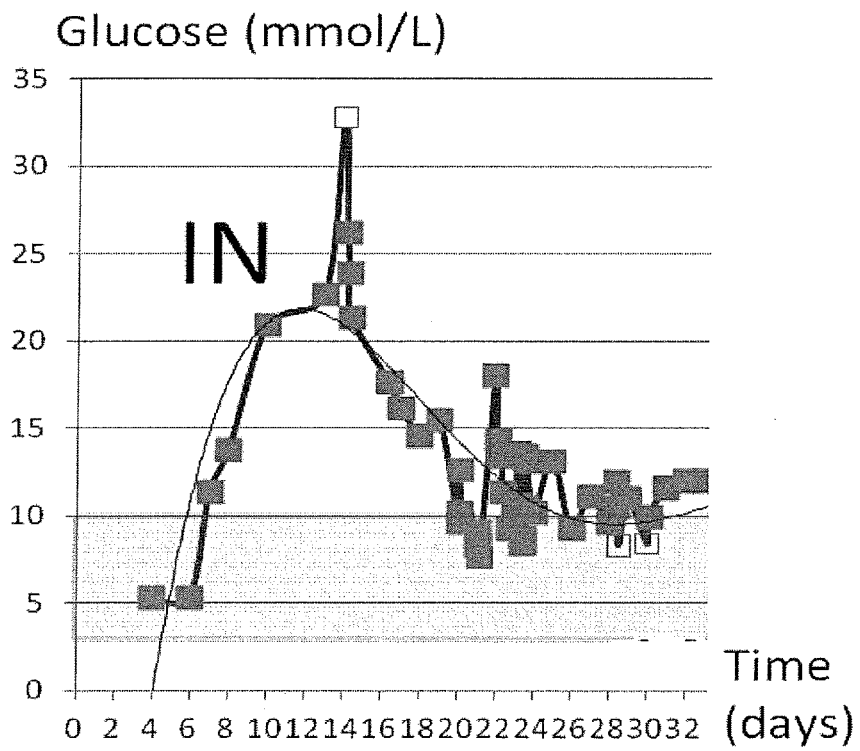
FIG. 6 shows the reduction of blood glucose basal levels in a pig model as described in Example 2.
Figure 7:
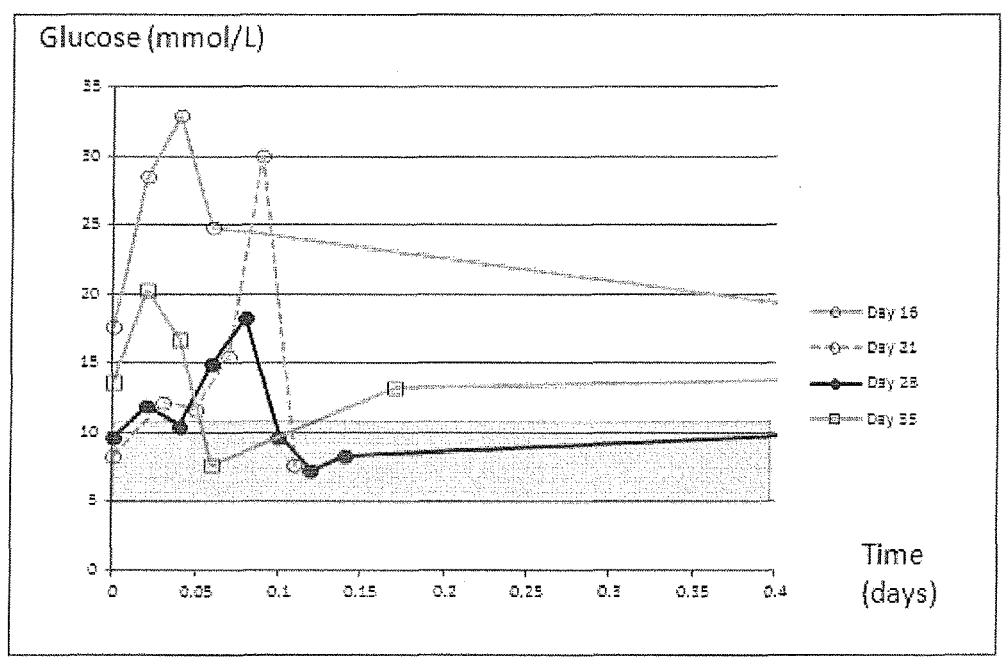
FIG. 7 shows the effect of closed loop adjustment on glucose challenges and how challenges were progressively better controlled in magnitude and at optimum, before removal of the insulin, within 30-40 min (ie 0.03 days).

The blood glucose was reduced from diabetic levels to closer to normal range on day 22, about six days after introduction of the insulin into the device (day 16) (see FIG. 6). During this time, oral glucose tolerance tests were progressively better controlled, such that although peaking at up to 20 mmol/L, they returned to normal within 30 min (FIG. 7).

The pig was at no time hypoglycaemic and had normal access to food and water, even during glucose challenges, gaining weight and in good health.

It had severe diabetes but was receiving optimum insulin with minimal excursions from the normal. Recovery of the diabetic state (not shown in Figures) indicates that pancreatic insulin was not responsible for the effect seen.

This Example demonstrates the successful implementation of a closed loop insulin delivery system, already shown to operate in vitro and in a rodent model. In this case, a refill system was designed in, with the advantage that the animal could be its own control. The success was dependent on the path length of the gel and the surface area for the exchanges in glucose and insulin to take place. It is likely that by making further adjustments, the blood glucose could be brought closer to the value accepted as a normal mean (5.4 mmol/L).

The system is shown to be suitable in terms of drug delivery to control diabetes symptoms in a man-sized animal.

While this invention has been particularly shown and described with references to preferred embodiments thereof, it will be understood by those skilled in the art that various changes in form and details may be made therein without departing from the scope of the invention encompassed by the appended claims.

The invention claimed is:

1. A container comprising a gel, wherein the gel comprises first and second gel forming moieties which bind reversibly to one another to form a gel, said binding being sensitive to the level of an analyte; the container allowing movement of the analyte into and out of the gel and being capable of resisting an internal pressure of at least about 250 mbar (25 kPa) to limit swelling of the gel caused by influx of water into the gel by osmosis,
   wherein the container comprises top and bottom walls joined by one or more side walls defining an enclosed space,
   the top wall comprising two or more substantially planar, inert metal grids and further comprising a porous membrane, and/or
   the bottom wall comprising two or more substantially planar, inert metal grids and further comprising a porous membrane,
   wherein the substantially planar, inert metal grids reinforce the structure of the container and restrict expansion of the gel, and further wherein the gel is contained within the enclosed space between the top wall and the bottom wall.

2. The container according to claim 1, wherein the analyte is glucose.

3. The container according to claim 2, wherein the first moiety is a lectin, and the second moiety is a gel-forming macromolecule which binds to the lectin.

4. The container according to claim 3, wherein the first moiety is concanavalin A and the second moiety is dextran.

5. The container according to claim 1, wherein the grids are made from titanium or stainless steel and the one or more side walls are made from polycarbonate.

6. The container according to claim 1, adapted to contain two separate layers of gel.

7. The container of claim 6, wherein the container comprises two or more pairs of grids between which each layer of gel can be contained.

8. The container of claim 1, wherein the upper wall comprises two or more pairs of grids and the bottom wall comprises two or more pairs of grids, and wherein the gel is contained between the top wall and the bottom wall.

9. The container of claim 8, wherein the porous membrane(s) is a cellulose membrane.

10. A container containing a gel, wherein
 (a) the gel comprises first and second gel forming moieties which bind reversibly to one another to form a gel, said binding being sensitive to the level of an analyte, and
 (b) the container allows movement of the analyte into and out of the gel and limits swelling of the gel caused by influx of water into the gel by osmosis,
 (c) wherein the container comprises top and bottom walls joined by one or more side walls defining an enclosed space, the top wall comprising two or more substantially planar, inert metal grids and further comprising a porous membrane, and/or the bottom wall comprising two or more substantially planar, inert metal grids, and further comprising a porous membrane wherein the substantially planar, inert metal grids reinforce the structure of the container and restrict expansion of the gel and further wherein the gel is contained within the enclosed space between the top and bottom walls.

11. The container of claim 10, wherein the container is capable of resisting an internal pressure of at least about 250 mbar (25 kPa).

12. The container according to claim 10, wherein the gel is formed in a flat layer having a thickness of no more than about 2 mm.

13. The method of claim 12, wherein the gel is formed in a flat layer having a thickness of no more than about 1 mm.

14. The container according to claim 10, wherein the gel forms a relative barrier to a reservoir of an agent in the gel state, but in the sol state allows the agent to be released, and wherein the container is permeable to the agent.

15. The container according to claim 14, wherein the agent is a drug.

16. The container according to claim 15, wherein the drug is insulin.

17. The container of claim 10, wherein the upper wall comprises two or more pairs of grids and the bottom wall comprises two or more pairs of grids, and wherein the gel is contained between the top wall and the bottom wall.

18. The container according to claim 10, comprising two separate layers of gel, each layer of gel being contained between two or more pairs of grids.

* * * * *